United States Patent
Ting et al.

(10) Patent No.: US 10,332,625 B2
(45) Date of Patent: Jun. 25, 2019

(54) COORDINATING COMMUNICATIONS AMONG HEALTHCARE PROVIDERS

(71) Applicants: David M. T. Ting, Sudbury, MA (US); Eliot M. Rubinov, Palo Alto, CA (US); Mae-Ellen Gavin, Lexington, MA (US); Kyle Vernest, Boston, MA (US); Roelf Kuitse, Goshen, IN (US)

(72) Inventors: David M. T. Ting, Sudbury, MA (US); Eliot M. Rubinov, Palo Alto, CA (US); Mae-Ellen Gavin, Lexington, MA (US); Kyle Vernest, Boston, MA (US); Roelf Kuitse, Goshen, IN (US)

(73) Assignee: IMPRIVATA, INC., Lexington, MA (US)

( * ) Notice: Subject to any disclaimer, the term of this patent is extended or adjusted under 35 U.S.C. 154(b) by 963 days.

(21) Appl. No.: 14/680,590

(22) Filed: Apr. 7, 2015

(65) Prior Publication Data
US 2015/0332011 A1    Nov. 19, 2015

Related U.S. Application Data

(60) Provisional application No. 61/976,138, filed on Apr. 7, 2014.

(51) Int. Cl.
*G06F 19/00* (2018.01)
*G16H 40/20* (2018.01)
*G16H 80/00* (2018.01)

(52) U.S. Cl.
CPC ......... *G16H 40/20* (2018.01); *G06F 19/3418* (2013.01); *G16H 80/00* (2018.01)

(58) Field of Classification Search
None
See application file for complete search history.

(56) References Cited

U.S. PATENT DOCUMENTS

| | | | |
|---|---|---|---|
| 9,058,635 B1 * | 6/2015 | Rybkin | G06Q 50/24 |
| 2010/0114596 A1 | 5/2010 | Williams et al. | |
| 2012/0101849 A1 | 4/2012 | Mathur et al. | |
| 2013/0191161 A1 | 7/2013 | Churchwell et al. | |
| 2013/0317840 A1 * | 11/2013 | Creswell | G06Q 50/22 |
| | | | 705/2 |
| 2013/0317858 A1 | 11/2013 | Hasan et al. | |

(Continued)

FOREIGN PATENT DOCUMENTS

| | | |
|---|---|---|
| WO | WO-2001086575 A2 | 11/2001 |
| WO | WO-2008133842 A1 | 4/2008 |

OTHER PUBLICATIONS

Pankaj et al, Team Assignment System: Expediting Emergency Department Care, Annals of Emergency Medicine, p. 499, vol. 46, 2005 (Year: 2005).*

*Primary Examiner* — Dennis W Ruhl
*Assistant Examiner* — William G Lultschik
(74) *Attorney, Agent, or Firm* — Morgan, Lewis & Bockius LLP

(57) ABSTRACT

Computer-implemented systems and methods automatically track the dynamic composition of a patient-care team by combining and harvesting information from at least two electronic audit trails: (1) a trail recording access to electronic medical records (EMR), e.g., read-access to patient data, electronic prescriptions and physician orders, etc., and (2) a trail recording electronic communications (email, text messages, etc.) regarding and referencing the patient.

34 Claims, 3 Drawing Sheets

(56) References Cited

U.S. PATENT DOCUMENTS

| | | |
|---|---|---|
| 2013/0325499 A1 | 12/2013 | Kohane |
| 2013/0325503 A1 | 12/2013 | Abrahams et al. |
| 2014/0039912 A1 | 2/2014 | Turinas et al. |
| 2014/0164011 A1* | 6/2014 | Guelich ................ G06F 19/327 705/2 |
| 2015/0234990 A1* | 8/2015 | Patadia ................ G06F 19/327 705/2 |

* cited by examiner

COORDINATING COMMUNICATIONS AMONG HEALTHCARE PROVIDERS

CROSS-REFERENCE TO RELATED APPLICATIONS

This application claims priority to and the benefit of U.S. Provisional Application No. 61/976,138, filed on Apr. 7, 2014, the entire disclosure of which is hereby incorporated by reference.

TECHNICAL FIELD

The invention relates generally to systems and methods for coordinating communications among a team of healthcare providers.

BACKGROUND

In typical healthcare settings, the care team for a particular patient is dynamic, i.e., clinicians frequently join and leave the team and responsibility for the patient may shift among team members depending on, e.g., their availability and the evolving needs of the patient. For instance, in addition to a primary physician and/or one or more nurses who are involved in the care of the patient for an extended period of time, the team may include a number of specialists (e.g., a cardiologist, anesthesiologist, etc.) who have only one or few interactions with the patient. As another example, a patient-intake team or emergency-room personnel may initially capture important patient information and/or provide urgent care, but later hand the patient off to another group of clinicians and cease involvement with the patient. The clinicians who are actively involved in the patient's care at a particular time and/or who should be kept abreast of the patient's condition can be difficult to track, compromising the ability of a team member to identify the individuals who should receive certain patient-related communications.

The difficulty of tracking team members responsible, at a given time, for a particular patient carries administrative as well as clinical implications. Healthcare regulations mandate that "protected health information" (PHI) be accessible only by caregivers authorized to access the information. Proper user authentication is required to access and alter PHI; this not only ensures patient privacy and safety, but also permits changes made to patient records to be audited later.

Accordingly, there is a need for systems and techniques for tracking a patient's care team over time, and for assessing, at any given time, a given clinician's degree of involvement with the patient.

SUMMARY

The present invention provides a computer-implemented system and methods for automatically tracking the dynamic composition of a patient-care team by combining and harvesting information from one or more of at least three electronic audit trails: (1) a trail recording access to electronic medical records (EMR), e.g., read-access to patient data, electronic prescriptions and physician orders, etc., (2) a trail recording electronic communications (email, text messages, etc.) regarding and referencing the patient, and (3) an event-based trail, e.g., system-generated alerts notifying personnel of the availability of a lab result for a patient or the admission into the facility of a patient linked in EMR to alert recipients. The first type of information is routinely recorded in secure computer systems based on users' log-ins and access requests, and is confined to the authorized system users within an organization (such as a hospital). The second type of information, by contrast, may reach outside the organization and capture, e.g., communications between clinicians at a hospital and outside clinical specialists who are consulted on particular medical issues. In some embodiments, the system also captures additional information indicative of patient care, such as a provider's physical entrance into the patient's room as detected, e.g., by a wireless reader and/or messages from the patient to a care provider. For each event recorded within the audit trails, the system typically stores a patient identifier, a provider identifier, and a time stamp (and possibly the location of the provider at the time of the event, or substantive information such as contents of a message, accessed record and/or patient location). This allows the system to generate, for each patient, a timeline of who participated in the patient's care when (and possibly where, how, etc.).

From the audit information, a level of involvement with the patient may be inferred for each care provider. This data, in turn, facilitates automatically identifying the members of the current team, and the scope of the team can be defined based on particular needs under given circumstances. For example, in its broadest scope, the team may include everyone who is or was involved in the patient's care at any time. In many situations, however, the relevant team may include only those providers who have cared for the patient within some suitably defined time period (e.g., within the past three days), or only those who have dealt with a particular medical condition of the patient (e.g., only heart specialists). A care provider who needs to communicate with his colleagues may send a message to all members within the current team (using, e.g., a default team-scope definition, choosing between multiple pre-defined team-scope definitions, or customizing the team-scope definition manually—e.g., by specifying a time period during which a provider must have interacted with the patient to be considered a member of the current team) without the need to select the individual recipients of the message manually. Interaction with a patient may be registered in one or more of various ways (short of a formal, recorded association), e.g., a clinician accessing a patient's medical records, ordering a test, or even entering the patient's room (which may be recorded by a wireless reader); again, the degree of patient interaction necessary for team membership may depend on the patient's condition, institutional policy, user (e.g., clinician) selection, or other criteria. In some embodiments, the system also allows determining the current locations of the team members and, optionally, tailoring the list of recipients based thereon.

In some embodiments, the definition of the care team may even be expanded to include people only potentially rather than actually involved with the patient. For instance, an interaction of the cardiologist with the patient a couple of days ago may indicate that cardiology is relevant to the patient, and the team may, accordingly, be defined to include all members of the cardiology unit present in the hospital on a particular day and thus available to attend to the patient should the need arise. More generally, personnel relationships may also be used to expand the team—for example, involvement of a specialist may result in inclusion of the specialist's group, support staff, etc. The point is that the way the "team" is assembled is flexible and can be tiered into, say, a primary tier of people directly involved and a secondary tier of less-involved but still-relevant clinicians for backup purposes.

Accordingly, in a first aspect, the invention pertains to a method of facilitating communication among personnel responsible for care of a patient. In various embodiments, the method comprises the steps of providing, at an audit server, access to a database comprising records relating patients to a master list of healthcare personnel, the master list of personnel corresponding to a plurality of patient care teams each associated with a patient; detecting, by the audit server, an activity indicative of responsibility for care of the patient by a person not listed in the patient care team corresponding to the patient; revising, by the audit server, the patient care team list in the record corresponding to the patient by adding personnel identifiers to, or removing personnel identifiers from, the patient care team list; communicating, by the audit server via a network, an update to the patient care team list to an application running on a communication device of each member of the patient care team; and causing a communication to be sent, by a communication device of a member of the patient care team, to all other listed members of the patient care team upon selection of the corresponding patient.

In various embodiments, the update is a revised patient care team list. The audit server may revise the patient care team list in response to an event, in response to the passage of time, in accordance with a rule, and/or in response to a message received from a caregiver. In some embodiments, the audit server comprises an interface for receiving data from an external source and/or a polling module for polling an external resource for data, the rule being activated by received data.

In some embodiments, the method further involves creating, at a communication device of a member of the patient care team, a message designating the care team a recipient; in response to the designation, obtaining, at the communication device, the patient care team list; and communicating, via a network, the message to devices associated with the members of the patient care team.

The method may also involve detecting, at the communication device, an activity indicative of responsibility for care of the patient by a person not listed in the patient care team corresponding to the patient; adding, by the device, an identifier of the person to the patient care team list to update the list; and communicating, by the device, the update to the audit server.

In another aspect, the invention pertains to a system facilitating communication among personnel responsible for care of a patient. In various embodiments, the system comprises an audit server that itself comprises (i) a database comprising records relating patients to a master list of healthcare personnel associated with care of the patients, the master list of personnel corresponding to a plurality of patient care teams; and (ii) a processor configured to (A) detect activities indicative of responsibility for care of the patient by persons not listed in the patient care team corresponding to the patient, and (B) revise the patient care team list in the record corresponding to the patient by adding personnel identifiers to, or removing personnel identifiers from, the patient care team list. The system further comprises a plurality of communication devices each comprising (i) a database comprising records relating patients associated with an authorized user of the device to a list of healthcare personnel associated with care of the user-associated patients; and (ii) a processor for (A) receiving updates from the audit server, (B) in response thereto, adding or removing at least one member of the healthcare-personnel list, and (C) causing a communication to be sent to all other listed members of a patient care team upon selection of the user-associated corresponding patient.

In various embodiments, the update is a revised patient care team list. The audit server may revise the patient care team list in response to an event, in response to the passage of time, in accordance with a rule, and/or in response to a message received from a caregiver. In some embodiments, the audit server comprises an interface for receiving data from an external source and/or a polling module for polling an external resource for data, the rule being activated by received data.

In various embodiments, the processors of the communication devices are further configured to detect an activity indicative of responsibility for care of the patient by a person not listed in the patient care team corresponding to the patient; add an identifier of the person to the patient care team list; and communicate the update to the audit server.

The term "substantially" or "approximately" means ±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description, in particular when taken in conjunction with the drawings, in which.

DETAILED DESCRIPTION

In various embodiments, systems in accordance with the invention capture information about access to patient records and orders, communications related to a patient, and optionally other factors indicative of actual or potential involvement with the patient. This information is used to infer the current patient-care team (with variable definitions of team scope) and to facilitate targeted communications among the team members.

Figure 1A:
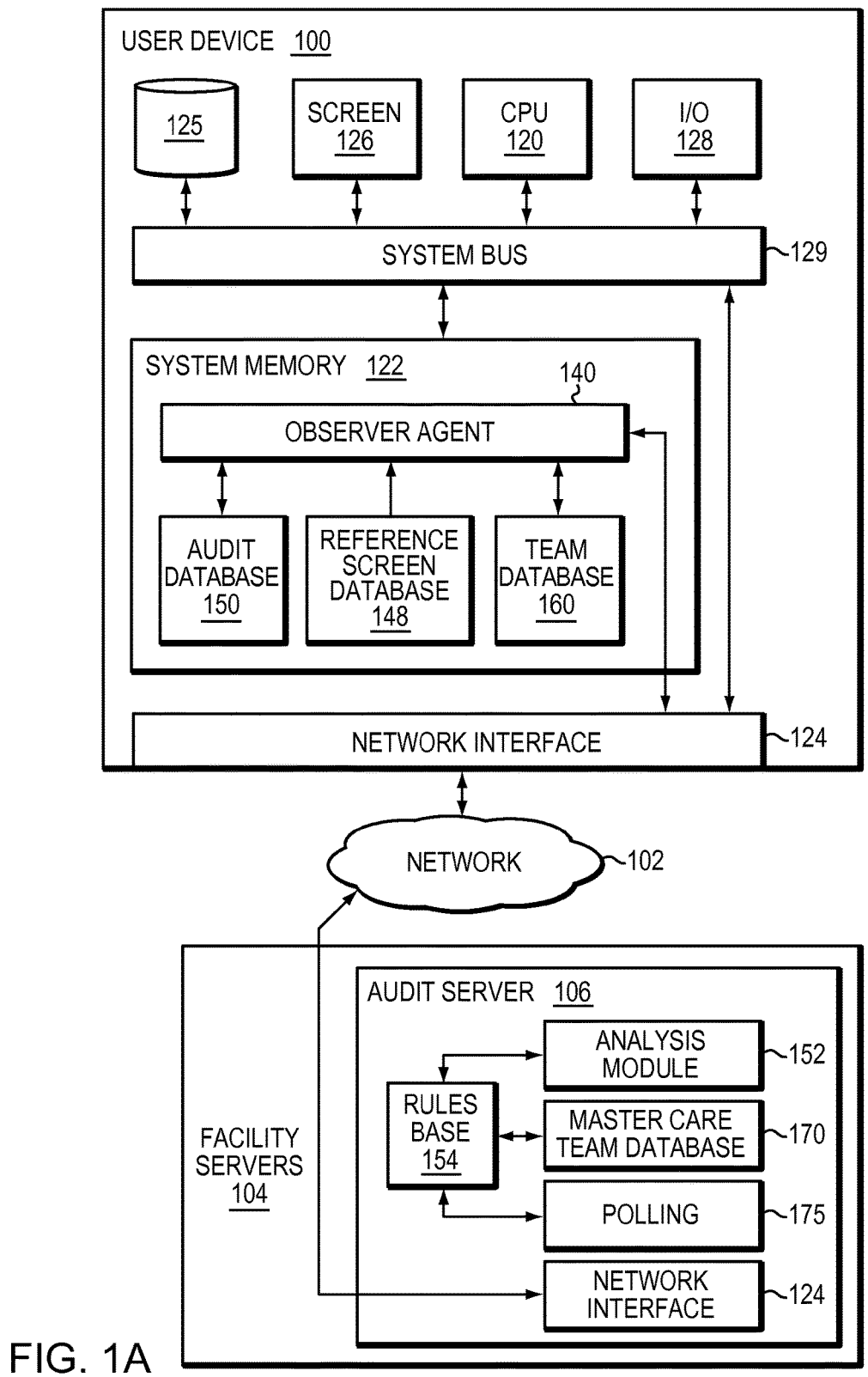
FIGS. 1A and 1B are block diagrams illustrating an exemplary system for maintaining, updating and exploiting patient caregiver lists in accordance with various embodiments.
Figure 1B:
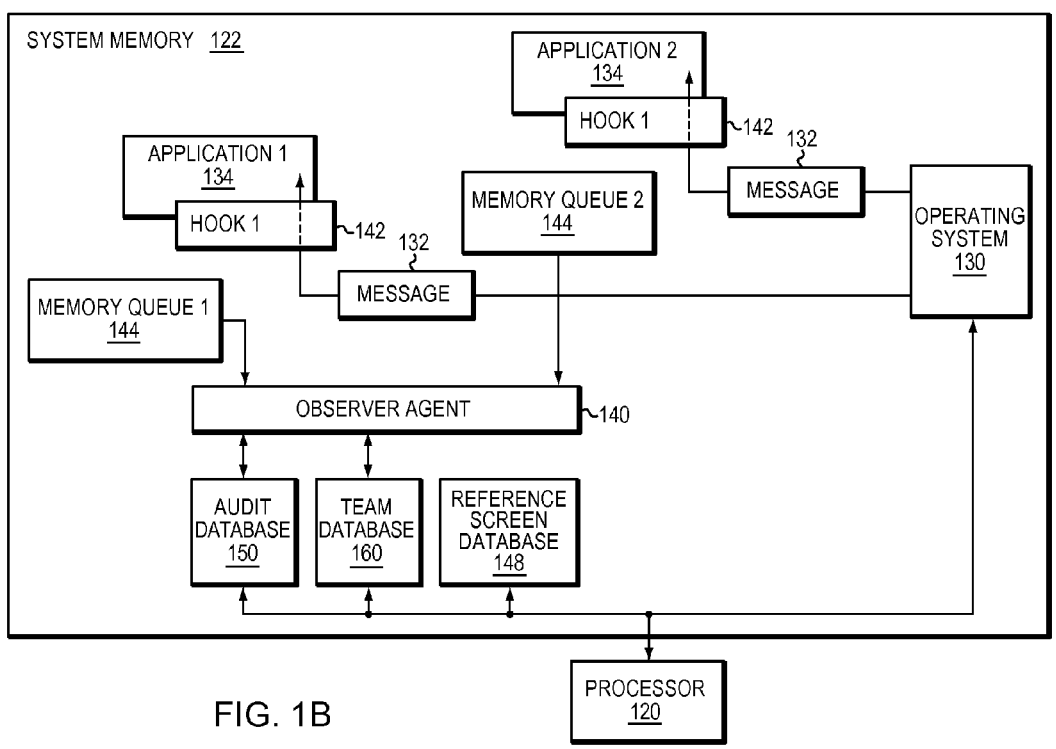

FIGS. 1A and 1B illustrate an exemplary hardware implementation. As shown in FIG. 1A, the system includes a plurality of user devices 100 connected, via a suitable wired or wireless network 102, to one or more servers 104. The user devices may be desktop or laptop computers, mobile phone, tablets, etc. —any computational device capable of running applications relating to clinical care of a patient. Typically, such devices will have authentication modalities to ensure access to PHI and secure applications by appropriate personnel.

The network 102 may, e.g., be the hospital's (or other organization's) intranet, and may be implemented as a local-area network (using, e.g., Ethernet or Wi-Fi technology). In a hospital context, the server(s) 104 may include, for instance, an authentication server that checks user's authentication credentials upon login to the system, a central data server (or group of servers) hosting the EMR databases, and/or one or more remote application-hosting servers. In embodiments hereof, the server(s) 104 include an audit server 106 for gathering and analyzing information from audit trails as described below. More generally, the various devices 100 may communicate with the servers 104 via a variety of modalities, e.g., via the Internet in a "cloud" configuration, via the telecommunications infrastructure in the case of mobile phones, or in any other suitable fashion. As explained in greater detail below, the network 102 may be any combination of local, wide-area and telecommunication networks facilitating communication between clinician devices 100 and the servers 104. For purposes hereof, the critical feature is not the modality of device-to-server communication but the ability of the audit server 106 to receive or monitor information streams relevant to the changing identities of patient-care providers.

Similarly, the device 100 (sometimes called a "communication device") may be any computational entity running suitable software, and typically includes a processor 120 (e.g., a CPU) and associated system memory 122, a network interface 124, and, usually, one or more non-volatile digital storage media 125 (such as a hard disk, CD, DVD, USB memory key, etc.) and associated drives. Further, the workstation 100 includes user input/output devices such as a display screen 126, conventional tactile input devices 128 such as keyboard and mouse or touch pad, and optionally microphone and speaker, cameras (e.g., for user authentication and detection of walk-away events), etc. The various components communicate with each other via one or more bidirectional buses 130.

In use, the processor 120 executes one or more computer programs (herein conceptually illustrated as program modules) stored in the system memory 122. With reference to FIG. 1B, an operating system 130 (such as, e.g., MICROSOFT WINDOWS, UNIX, LINUX, iOS, or ANDROID) provides low-level system functions, such as file management, resource allocation, and routing of messages 132 from and to the hardware devices (such as the user input/output devices 126, 128) and one or more higher-level user applications 134 (such as EMR applications, office programs, a web browser, etc.). The user interacts with the application(s) 134 by providing input via the input devices, e.g., by typing on the keyboard, moving the mouse, or clicking with the mouse on a displayed control element such as a scroll bar. In a WINDOWS system, for each such input event, a message 132 is created (e.g., by the device driver of the input device). Messages 132 may also be created by and/or in response to applications 134; for example, an application 134 may send a message containing an output to be displayed on the screen 126, or effect a system-level change such as a change to the pool of system font resources or window resizing. The MICROSOFT WINDOWS operating system passes all application-related inputs in the form of messages 132 to the window(s) in which the application 134 operates; each message 132 may, for this purpose, include a window handle specifying the destination application or window. The message 132 may further include a message identifier that tells a so-called window procedure of the destination window how to process the message, as well as one or more message parameters containing relevant data (or a pointer thereto) used during such processing. Each message 132, depending on its type, is either sent directly to the windows procedure, or temporarily stored in a message queue for the destination application or window for subsequent retrieval therefrom by the window procedure.

The device 100 may utilize a software observer "agent" 140—i.e., an application typically running as a background process (invisibly to the user)—that identifies patients located in the course of a clinician's use of computer applications 134. The agent 140 may authenticate the user and then monitor the system for specific application screens. The agent 140 may track various events generated by each application 134 that the user employs (such as when a screen is ready to be made visible or when it is being dismissed), as well as how the user interacts with the controls on each screen, by, for example, hooking into the message queue for different applications. As understood by those skilled in the art, the message queue allows system hardware to pass input to the operating system on an event-driven basis. The MICROSOFT WINDOWS operating system passes all application-related inputs to the window(s) in which the application operates. Each window has a function, called a window procedure, that the operating system calls whenever it has input for the window. The window procedure processes the input and returns control to the operating system. The observer agent 140 may be implemented as an application that is started like any other application but does not create a user interface, or as a system service that is started automatically upon boot-up of the device 100. As shown, the agent 140 may generate, for each monitored application 134, a separate "hook" 142 operating within the context and address space of that application. The hook 142 non-intrusively intercepts messages 132 (corresponding to events) received by any window associated with the hooked application, and logs the corresponding events in a memory queue 144. The observer agent 140 may subsequently, e.g., when the application 134 is idle, read out the memory queue 144; this arrangement minimizes performance impacts on the user. Application-hooking technology that, in this manner, allows an external application such as the observer agent 140 to be injected into another application to monitor messages passed between that application and the operating system is routinely provided by, e.g., the WINDOWS operating system, where it ordinarily serves debugging, shadowing, training, and similar functions.

The observer agent 140 may compare the event-related screen data against a database 148 of reference screens, i.e., identification data for individual screens (including the entire screen contents or portions thereof), which may be structured, e.g., within a declarative XML document. The reference-screen database 148 may be centrally stored on one of the servers 104 and then downloaded to different devices 100 when the associated observer agent 140 starts up, e.g., following user log-on. Alternatively, the database 148 may be stored on permanent storage media 125 within the device 100. For efficient access, the database 148 is typically (but not necessarily) loaded into the system memory 122 in its entirety upon launch of the observer agent 140. Based on comparisons of the event-related screen data with the reference screens, the agent 140 may filter screens and/or identify types of screens, e.g., for subsequent recognition of certain patterns. The observer agent 140 may also be configured to discriminate, e.g., based on the event identifiers, between generic, low-level events (such as, e.g., window-active, window-focus, window-resize events and other events generated by the operating system to indicate that the screen is active) and "significant" events that warrant screen comparison; in other words, the agent may perform an initial coarse filtering before primary filtering by comparing the information on the screen against the reference set of screens in the database 148.

In particular, the agent 140 detects screens used to locate and select a patient, and registers the identity of the patient (e.g., by medical reference number (MRN), full name and date of birth) as captured from the application—either by interrogating the WINDOWS controls or reconstituting the information from the screen display commands (i.e., GDI interception)—in the audit database 150, which accumulates events and associates them with patient identifiers. In particular, the patient identifier, the application name, the user's ID, a timestamp, together with the machine identifier (hostname or MAC address), and recorded events are combined into a database record in the database 150. Events often originate with applications active in one of at least three audit trails: requests for access to EMR (e.g., read-access to patient data, electronic prescriptions and physician orders, etc.), electronic communications (email, text messages, etc.) regarding and referencing the patient, "push" notifications of events such as readiness of lab results or entry into the facility of a particular clinician's patient.

In some embodiments, some initial processing is performed at the device 100 i.e., the agent 140 is programmed to recognize certain events as mandating additions to a team database 160, which locally maintains a current list of healthcare providers associated with patients whom the device user is treating (i.e., those patient's to whom the user has data access pursuant to the facility's patient-privacy rules). In other embodiments, only the records of the master care team database 170 maintained by the audit server 106 are updated. In such implementations, records from the audit database 150 are sent individually or in batches to the audit server 106, which uses them to update the master care team database 170; the audit server 106 creates and updates the individual team databases 160 from the master database 170.

In any case, the patients of the user of the device 100 are tracked and may be associated with that user; for example, the team database 160 may be organized as a relational database so that received patient-selection information may be aggregated and indexed for rapid retrieval using, for example, either the patient identifier or the user's ID. Timestamps are assumed to be synchronized across different machines (and time zones) so that a patient timeline can be properly reconstructed. In some embodiments, the agent monitors only applications known to involve access to EMR. Patient-clinician associations may also be obtained via direct interactions with various medical application software programs such as EMR, Lab Information Systems (LIS), Picture Archiving and Communications Systems (PACS), or business systems (e.g., b means of direct API calls to their application or severs) or via access to audit records produced by these systems. Audit information may also be obtained via "listeners" to system messages generated by these applications using HL7 (High Level 7) exchanges. In addition, it is possible for a facility server 104 to aggregate email, texting and notification/alert records generated either by local or remote (e.g., cloud-hosted) servers. In the case of communication systems that are "patient-centric" (i.e., where the subject line already includes the patient's medical record number), the association between sender, receiver and patient is already known and available to be retrieved by the facility server 104.

In a similar manner, patients who should be associated with particular clinicians may be identified from mobile texting or email applications 134 when clinicians communicate with each other regarding a patient. In particular, the identifier of a patient identified in a message, as well as the names of the sender and recipients, can be obtained by the agent 140 either directly from the mobile application or on the routing server (in the cloud or locally) if the application 134 has the ability to open the payload containing the actual message. (It should be noted that if messages are routed to a virtual, on-call specialist, as is the case in some systems, the agent 140 converts the virtual role to the named individual with that role.) Each time a new message is created (or responded to), the agent 140 updates the database 150 with the relevant patient/clinician use data. Finally, healthcare providers' email applications may be configured to recognize patient names in order to identify incoming emails from patients. Such emails may be indicative of provider involvement with the sending patient, so that based on the analysis described below, the provider may be placed on the patient's care team.

Accumulated audit records over time provide important statistics on the association between patients and clinicians that can be used as the basis for identifying a patient team. This association is assessed by an analysis program or module 152, running on the audit server 106 and executed by a conventional processor 153, as new audit database records are received. Again, the analysis module 152 may be solely responsible for maintaining all patient teams for all devices 100, or may share this responsibility with the observer agents 140 of the devices 100. (Indeed, if desired, the functionality of the analysis module 152 can be implemented on the devices 100 rather than on a central server. Moreover, observation agents may cache and hold interaction data for a period of time to reduce the traffic to the server 104.)

Statistical measures such as number of interactions over a time period or the aggregate number of interactions by a clinician (i.e., via a clinician's device 100) about a patient can indicate complexity or severity of the patient's case, and can be used as filters (e.g., as a threshold to screen team members, or in order to identify and differentiate among different levels of association, e.g., a "core" team vs. an "extended" team). For example, clinicians with higher numbers of direct interactions (either cumulatively or over a predetermined time period—e.g., the prior hour, day, week, etc.) might be deemed to be part of the core team directly responsible for care of the patient at the present time, while those who merely receive text or email updates about the patient or only infrequently review the patient's EMR records may be considered part of the extended team (if at all). The significance of an observed frequency may take account of the nature of the clinician's responsibilities, some of which involve more frequent (but insignificant) communication than others. Interaction levels can also be gauged based on whether an outbound message with a response request embedded in the content is, in fact, responded to by the recipient. The time delay between receipt of the message and the response time may also indicate degree of urgency and, hence, bear on the interaction level. An immediate response, for example, would indicate direct involvement; a message that never receives a response, by contrast, may be ignored. Weighting may also be determined by clinician preference, e.g., an expressed preference in terms of weighting the relative importance of the number of interactions. A charge nurse sending out routine updates, for example, may want to reduce the significance of the interactions against his norm for the role, thus reducing his importance in the care of the patient (since the messages will mostly be non-critical updates). More generally, the rules may accommodate expressed clinician preferences that bias the "involvement index" (i.e., the significance accorded to particular activities) by adding corresponding weighting coefficients to the aggregate sum.

The makeup of the care team for the patient may be defined according to any suitable policy, which may vary among patients (depending on, for example, the nature of their conditions), among clinician specialties, with the time of day, or other relevant factor(s). The policy may be implemented in a set of rules stored in a rule base 154. For example, the care team may range from the set of all clinicians who had some interaction with the patient to only those who responded within some time interval of the initial encounter. Thus, the analysis program 152 may use scoring rules 154 to identify the core team and the extended team. A representative (though obviously incomplete) set of scoring rules is set forth in Table 1:

TABLE 1

| Event | Score |
| --- | --- |
| >3 emails containing patient name | if in previous hour: score = 50 |
| | if in previous 6 hours: score = 25 |
| | if in previous 24 hours: score = 15 |
| Patient condition | Acute care: multiply raw score by 2 |
| | Cardiac: multiply raw score by 1.5 |
| Patient location | ICU: multiply raw score by 2 |
| Diagnostic test | Sliding score depending on types and numbers of test ordered |

The score may be processed by a rules engine or decision engine to identify the core team. The rules and or thresholds used by the rules engine can be either predefined by an administrator, configured or modified by individual clinicians and/or learned by the system by observing individual usage patterns over time across many patients. A time-domain filter may be used to smooth out "noise" in the score data and can be either linear (e.g., a weighted time-averaged sum) or non-linear (e.g., a median filter), or weighted by a coefficient based on clinician preferences as noted above. The rules engine uses the "interaction score" for all clinicians associated with the patient to determine 1) who are members of the care team and 2) the degree of association. The interaction score may be presented in a visual format so that the degree of interaction can be easily seen—for example, those clinicians with higher scores may have more graphical bars associated with their names, or the names may be color coded to indicate the interaction score. This allows a sender to quickly determine who is closest to the patient.

In some embodiments, the analysis module 152 and/or the individual observer agents 140 identify a core team and an extended team in accordance with a policy—e.g., a score above a high threshold places the device user on the core team, while a score above a second, lower threshold places the device user on the extended team. Note that various of the rules have temporal components, and indeed, even those without explicit time limitations may be applied only if the referenced event has occurred recently enough (i.e., if the event triggering a rule is stale as specified in the rule itself, the rule is not applied).

The composition of a team (or the core and extended teams) may be maintained in the team database 160 on each of the devices 100 whose users are part of the care team. The database 160 may be push-updated periodically by the audit server 106 to keep the care teams associated with each patient in the device database 160 current based on the rules 154 and other considerations as discussed below. The update frequency is determined by a policy (e.g., daily or more frequently). Similarly, if the observer agents 140 of the devices are capable of augmenting and/or pruning the team database 160 on their own, revisions are pushed up to the audit server 106 (typically immediately so that the master team database 170 is never out of date).

The databases 160, 170 may be also manually edited to remove or add members. In various embodiments, care team members who receive updates about a patient with whom they are no longer associated can "opt out" and remove themselves from the master database 170 maintained by the audit server 106 and, ultimately, the various distributed databases 160. Alternatively, they may simply indicate that they no longer wish to be considered part of the care team.

Typically, the analysis program 152 independently keeps track of statistical data on patient affiliation to determine who is still engaged in active care of the patient; this functionality may be implemented in the rule base discussed above. For example, if a team member has not received or sent a message regarding a patient for a specified period of time, a rule may dictate that he be removed from the list. The relevant time, or even the appropriateness of pruning the list, may once again depend on the role typically played by a particular clinician in patient care (for example, the persistent absence of messages about a patient may be relevant to patient affiliation for some team members but not for others, and if the patient's condition remains acute, it may be important to maintain a stable team). The stored rules 154 define the time periods and other criteria applied to care team lists to keep them current.

Conversely, the rules 154 may augment the team beyond caregivers identified statistically or by scoring as described above. Most simply, simply sending a message to a care-team group may make the sender part of the care team; similarly, sending a message to a virtual role would include the assigned clinician (e.g., an on-call cardiologist) on the care team. In these systems, which embody some degree of automatic inclusion, it is up to an assigned clinician to determine whether she wants to continue to be considered a member of the team or to drop out.

Alternatively or in addition, inclusion policies may focus automatic inclusion on certain specialties. For example, for some acute-care specialties, addition of one group member to a care team list may result in automatic addition of all other group members (or group members at a particular facility, or on a particular floor). This may occur independent of a score, i.e., certain rules may bypass scoring and add a team based on a patient's condition and the current availability of appropriate team members (e.g., a full cardiac team after a patient suffers a cardiac event). Team members may also be changed independent of score depending on clinicians' changing availabilities; when a clinician on the team travels or is otherwise unavailable on a particular day, the analysis program 152 may replace the unavailable clinician on the team roster(s) by another clinician. The rules 154 may, for example, ensure that at least one member of a particular care group is associated with the patient at all times. In such cases, the audit server 106 may keep track of which clinicians are actually at the facility (by, for example, querying the building's card-entry system, examining log-on and log-off records, etc.) and alter the care team list accordingly, in real-time. Alternatively, a scheduling system tracks availability status may be employed. For example, a surgeon may be part of a care team but may want to opt out when he is unavailable (e.g., while he is in the operating room or not on call). This and other polling tasks may be handled by a polling module 175. The server 106, like the devices 100, has a network interface 124 for communication.

Care team information can be leveraged in a number of different ways to make it easier for clinicians to track the patients they are caring for and to communicate with other members of the care team. With, for example, core and extended teams defined for each of the patients listed in the records of the team database of a device 100, the user may direct a new email or text message simply to the core care team or to the extended care team for a particular patient. This capability may operate by defining a recipient list in, for example, a helper application running on the clinician's mobile device that operates with email or texting applications, and which draws data from the team database 160. The helper application may also allow the clinician to express preferences regarding team membership, including opting into or out of the care team for a particular patient.

The present invention can also be used to track patients rather than caregivers. For example, the audit information database 150 can be queried to find the list of all patients associated with a particular clinician over a specific period. This information can be used in various ways, e.g., to populate a shortcut bar on the user's desktop to launch specific EMR or PACS (Picture Archiving and Communications Systems) applications so they open to the designated patient, or simply as a shortcut to facilitate pasting the patient's MRN or other demographics (name, DOB, etc.) that are frequently entered into other applications. This reduces the inconvenience and potential errors associated with rekeying information.

Figure 2:
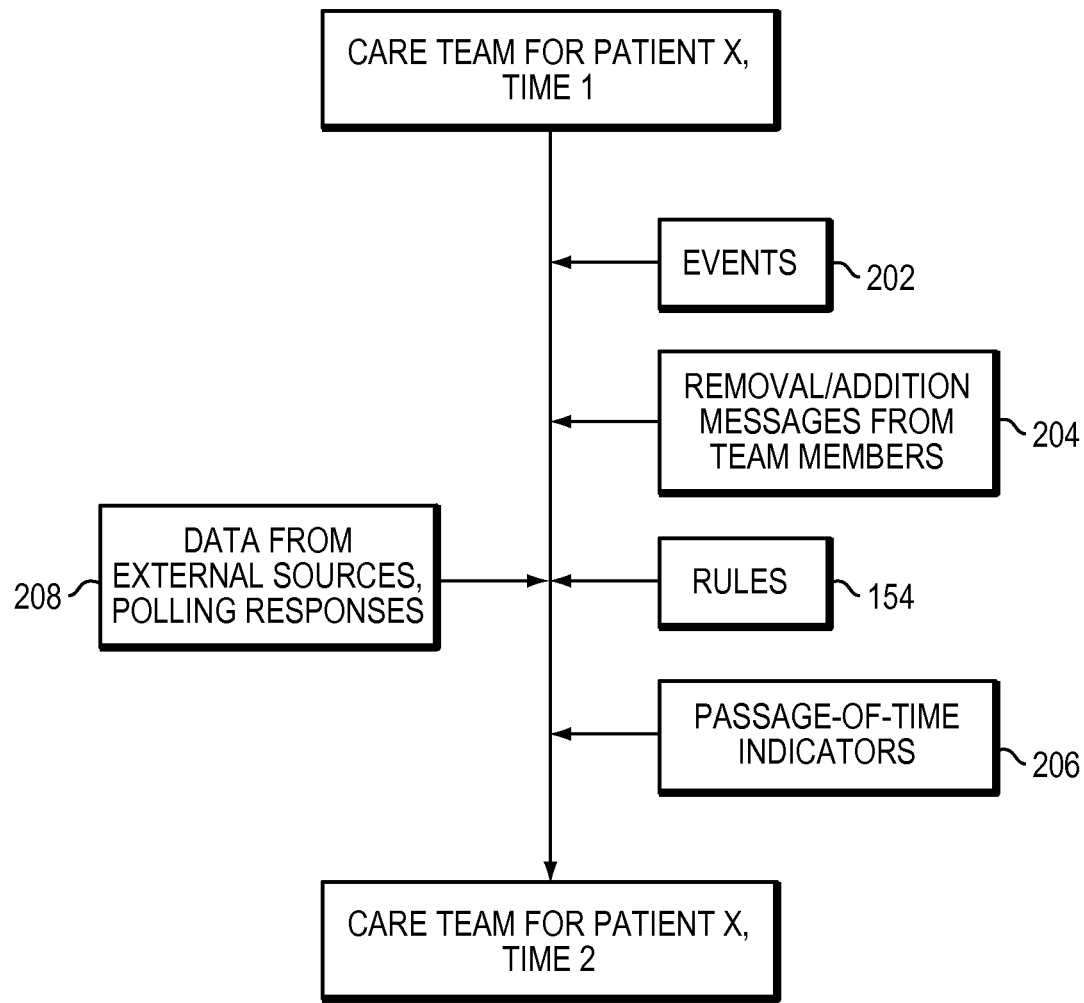
FIG. 2 is a workflow diagram illustrating factors involved in updating patient caregiver lists in accordance with various embodiments.

Refer now to FIG. 2, which illustrates the factors that influence and alter the composition of a care team for a given patient over time. Although the rules 154 may dominate the process of updating the care team, the system is not necessarily rules-based, and in any case, some transactions may operate outside the rules—for example, the rules may be overridden by an emergency event, which, in effect, triggers a universal set of "hard-wired" rules that supersedes any particular rules base 154. In any case, events 202, such as sending or receiving a message, or accessing EMR, can result in the addition of members to the relevant care team record maintained in the databases 160. Caregivers may also directly request that they be added to or removed from the team list for a particular patient as indicated at 204. The passage of time, indicated at 206, may cause pruning of the care team depending on the patient's status and a clinician's role in patient care; for example, a sufficient elapsed time since the last patient-related activity may justify removal of a clinician from the team database record. Data 208 from external sources, such as incoming test results or messages, may result in alteration of a patient's care team. Furthermore, the audit server 106 and/or devices 100 may be programmed to periodically poll sources of critical information, such as a facility's perimeter access system, log-on/log-off records, and/or scheduling systems to determine whether existing members of the care team are, in fact, on site. The departure of a critical team member from the facility for the day, or the addition of a team member whose presence implies the need for collateral team members, may trigger revision of the patient's care team in the database 160.

As noted above, the audit server 106 communicates with the devices 100 via a computer or telecommunications network. The term "network" is herein used broadly to connote wired or wireless networks of computers or telecommunications devices (such as wired or wireless telephones, tablets, etc.). For example, a computer network may be a local area network (LAN), a wide area network (WAN), or devices intercommunicating using neaer-field communication. When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), Bluetooth, Zigbee, IrDa or other suitable protocol. Furthermore, components of the system may communicate through a combination of wired or wireless paths, and communication may involve both computer and telecommunications networks. For example, a user may establish communication with an authentication server using a "smart phone" via a cellular carrier's network and authenticate by voice recognition over a voice channel; alternatively, she may use the same smart phone to authenticate to the same server via the Internet, using TCP/IP over the carrier's switch network or via Wi-Fi and a computer network connected to the Internet.

Any suitable programming language may be used to implement without undue experimentation the functionality described above. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript for example. Further, it is not necessary that a single type of instruction or programming language be utilized in conjunction with the operation of the system and method of the invention. Rather, any number of different programming languages may be utilized as is necessary or desirable.

The audit server 106 may also include other removable/nonremovable, volatile/nonvolatile computer storage media. For example, a hard disk drive may read or write to nonremovable, nonvolatile magnetic media. A magnetic disk drive may read from or writes to a removable, nonvolatile magnetic disk, and an optical disk drive may read from or write to a removable, nonvolatile optical disk such as a CD-ROM or other optical media. Other removable/nonremovable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The storage media are typically connected to the system bus through a removable or non-removable memory interface.

The processing units that execute commands and instructions may be general-purpose processors, but may utilize any of a wide variety of other technologies including special-purpose hardware, a microcomputer, mini-computer, mainframe computer, programmed microprocessor, microcontroller, peripheral integrated circuit element, a CSIC (customer-specific integrated circuit), ASIC (application-specific integrated circuit), a logic circuit, a digital signal processor, a programmable logic device such as an FPGA (field-programmable gate array), PLD (programmable logic device), PLA (programmable logic array), RFID processor, smart chip, or any other device or arrangement of devices that is capable of implementing the steps of the processes of the invention.

Although the invention has been described herein with respect to specific embodiments and details, various modifications, alternative embodiments, and different combinations of features that still solve the problems addressed by the invention in a similar manner will be readily apparent to a person of skill in the art, and are understood to be within the scope of the invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

Although the invention has been described herein with respect to specific embodiments and details, various modifications, alternative embodiments, and different combinations of features that still solve the problems addressed by the invention in a similar manner will be readily apparent to a person of skill in the art, and are understood to be within the scope of the invention.

What is claimed is:

1. A method of facilitating communication among personnel responsible for care of a patient, the method comprising the steps of:
    a. providing, at an audit server, access to (A) a database comprising records relating patients to a master list of healthcare personnel, each patient in the database being associated with (i) a core patient care team and (ii) an extended patient care team different from the core patient care team, the core patient care team and the extended patient care team being drawn from the master list of personnel, and (B) an involvement index assigning weights to activities indicative of responsibility for care of patients at least on the basis of a significance of the activity and a temporal component of the activity;
    b. cooperatively detecting, by the audit server and an observer agent, an activity indicative of responsibility for care of the patient by a person listed in the master list of healthcare personnel, wherein the observer agent monitors and automatically identifies screens (i) displayed on a communication device of the person, (ii) generated by one or more applications employed by the person, and (iii) identifying the patient;
    c. updating, by the audit server, an interaction score of the person based on the detected activity and the involvement index;
    d. revising, by the audit server and at least on the basis of the updated interaction score, the core patient care team list and/or the extended patient care team list in the record corresponding to the patient by (i) adding the person to the core patient care team list or the extended patient care team list, (ii) removing the person from the core patient care team list or the extended patient care team list, or (iii) moving the person from one of the core patient care team list or the extended patient care team list to the other;
    e. communicating, by the audit server via a network, an update to the core patient care team list and/or an update to the extended patient care team list to an application running on a communication device of each member of the core and/or extended patient care teams; and
    f. causing a communication to be sent, by a first communication device of a member of the core patient care team or the extended patient care team, to all other listed members of the core patient care team and/or the extended patient care team upon selection of the corresponding patient.

2. The method of claim 1, wherein (i) the update to the core patient care team list is a revised core patient care team list, and (ii) the update to the extended patient care team list is a revised extended patient care team list.

3. The method of claim 2, wherein the audit server revises the core patient care team list and/or the extended patient care team list in response to an event.

4. The method of claim 2, wherein the audit server revises the core patient care team list and/or the extended patient care team list in response to the passage of time.

5. The method of claim 2, wherein the audit server revises the core patient care team list and/or the extended patient care team list in accordance with a rule.

6. The method of claim 5, wherein the audit server comprises an interface for receiving data from an external source, the rule being activated by the received data.

7. The method of claim 5, wherein the audit server comprises a polling module for polling an external resource for data, the rule being activated by the data.

8. The method of claim 2, wherein the audit server revises the core patient care team list and/or the extended patient care team list in response to a message received from a caregiver.

9. The method of claim 1, further comprising the steps of:
    a. creating, at a second communication device of a member of the core patient care team list and/or the extended patient care team, a message designating the core patient care team list and/or the extended patient care team as a recipient;
    b. in response to the designation, obtaining, at the second communication device, the core patient care team list and/or the extended patient care team list; and
    c. communicating, via a network, the message to devices associated with the members of the core patient care team and/or the extended patient care team.

10. The method of claim 1, further comprising:
    a. detecting, at a second communication device of the member of the core patient care team or the extended patient care team, an activity indicative of responsibility for care of the patient by a person not listed in the core patient care team or the extended patient care team corresponding to the patient;

b. adding, by the second communication device, an identifier of the person to the core patient care team list or the extended patient care team list to update the list; and c. communicating, by the second communication device, the update to the audit server.

11. The method of claim 1, wherein revising the core patient care team list and/or the extended patient care team list comprises:

comparing the updated interaction score to a first threshold and a second threshold lower than the first threshold;

when the updated interaction score exceeds the first threshold, ensuring that the person is on the core patient care team associated with the patient;

when the updated interaction score exceeds the second threshold but not the first threshold, ensuring that the person is on the extended patient care team associated with the patient but not the core patient care team associated with the patient; and when the updated interaction score does not exceed the second threshold, ensuring that the person is not on the core patient care team associated with the patient or the extended patient care team associated with the patient.

12. The method of claim 1, wherein the involvement index assigns weights to activities on the basis of preferences of healthcare personnel.

13. The method of claim 1, further comprising causing to be displayed (i) at least a portion of the core patient care team list and/or at least a portion of the extended patient care team list and (ii) a visual representation of the interaction score of each member of the displayed at least a portion of the core patient care team list and/or at least a portion of the extended patient care team list.

14. The method of claim 1, further comprising, when the person is added to the core patient care team list or the extended patient care team list, automatically, by the audit server, adding one or more additional people to the core patient care team list or the extended patient care team list irrespective of interaction scores of the one or more additional people.

15. The method of claim 1, further comprising, when a member of the core patient care team list or the extended patient care team list is unavailable, adding, by the audit server, a replacement member to the core patient care team list or the extended patient care team list irrespective of an interaction score of the replacement member.

16. The method of claim 1, wherein the observer agent identifies screens, at least in part, by hooking into a message queue for each of the one or more applications employed by the person.

17. The method of claim 1, wherein the observer agent identifies screens, at least in part, by comparing screen data against a database of reference screens.

18. A system facilitating communication among personnel responsible for care of a patient, the system comprising:

a. an audit server comprising:
i. a database comprising records relating patients to a master list of healthcare personnel associated with care of the patients, each patient in the database being associated with (A) a core patient care team and (B) an extended patient care team different from the core patient care team, the core patient care team and the extended patient care team being drawn from the master list of personnel;

ii. an involvement index assigning weights to activities indicative of responsibility for care of patients at least on the bases of a significance of the activity and a temporal component of the activity; and iii. a server processor configured to (A) cooperatively detect activities indicative of responsibility for care of a patient by a person listed in the master list of healthcare personnel, (B) update an interaction score of the person based on the detected activities and the involvement index, and (C) revise, at least on the basis of the updated interaction score, the core patient care team list and/or the extended patient care team list in the record corresponding to the patient by (i) adding the person to the core patient care team list or the extended patient care team list, (ii) removing the person from the core patient care team list or the extended patient care team list, or (iii) moving the person from one of the core patient care team list or the extended patient care team list to the other; and b. a plurality of communication devices each comprising:
i. a database comprising records relating patients associated with an authorized user of the device to, for each patient, the core patient care team associated with the patient and the extended patient care team associated with the patient;

ii. a device processor for (A) receiving updates from the audit server, (B) in response thereto, updating a core patient care team list and/or an extended patient care team list for one or more of the patients, and (C) causing a communication to be sent to all other listed members of the core patient care team and/or the extended patient care team upon selection of the user-associated corresponding patient;

iii. a display for displaying screens generated by one or more applications employed by the user of the device; and iv. an observer agent, executable by the device processor, for detecting, cooperatively with the audit server, activities indicative of responsibility for care of the patient by, at least in part, monitoring and automatically identifying screens (i) displayed on the display and (ii) identifying the patient.

19. The system of claim 18, wherein the updates are revised core patient care team lists and/or extended patient care team lists.

20. The system of claim 18, wherein the updates are revisions to the core patient care team lists and/or the extended patient care team lists.

21. The system of claim 18, wherein at least some of the activities are events.

22. The system of claim 18, wherein the processor of the audit server revises the core patient care team list and/or the extended patient care team list in response to the passage of time.

23. The system of claim 18, wherein the processor of the audit server revises the core patient care team list and/or the extended patient care team list in accordance with rules.

24. The system of claim 23, wherein the audit server comprises an interface for receiving data from an external source, at least some of the rules being activated by the received data.

25. The system of claim 23, wherein the audit server further comprises a polling module for polling an external resource for data, at least some of the rules being activated by the data.

26. The system of claim 18, wherein the audit server revises the core patient care team list and/or the extended patient care team list in response to a message received from a caregiver.

27. The system of claim 18, wherein the processors of the communication devices are further configured to:
   a. detect an activity indicative of responsibility for care of the patient by a person not listed in the core patient care team or the extended patient care team corresponding to the patient;
   b. add an identifier of the person to the core patient care team list or the extended patient care team list; and
   c. communicate the update to the audit server.

28. The system of claim 18, wherein the server processor is configured to revise the core patient care team list and/or the extended patient care team list by:
   comparing the updated interaction score to a first threshold and a second threshold lower than the first threshold;
   when the updated interaction score exceeds the first threshold, ensuring that the person is on the core patient care team associated with the patient;
   when the updated interaction score exceeds the second threshold but not the first threshold, ensuring that the person is on the extended patient care team associated with the patient but not the core patient care team associated with the patient; and
   when the updated interaction score does not exceed the second threshold, ensuring that the person is not on the core patient care team associated with the patient or the extended patient care team associated with the patient.

29. The system of claim 18, wherein the involvement index assigns weights to activities on the basis of preferences of healthcare personnel.

30. The system of claim 18, wherein each communication device is configured to display (i) at least a portion of the core patient care team list and/or at least a portion of the extended patient care team list and (ii) a visual representation of the interaction score of each member of the displayed at least a portion of the core patient care team list and/or at least a portion of the extended patient care team list.

31. The system of claim 18, wherein the server processor is configured to, when the person is added to the core patient care team list or the extended patient care team list, automatically add one or more additional people to the core patient care team list or the extended patient care team list irrespective of interaction scores of the one or more additional people.

32. The system of claim 18, wherein the server processor is configured to, when a member of the core patient care team list or the extended patient care team list is unavailable, add a replacement member to the core patient care team list or the extended patient care team list irrespective of an interaction score of the replacement member.

33. The system of claim 18, wherein the observer agent identifies screens, at least in part, by hooking into a message queue for each of the one or more applications employed by the user of the device.

34. The system of claim 18, wherein the observer agent identifies screens, at least in part, by comparing screen data against a database of reference screens.

* * * * *